United States Patent [19]

Schwob

[11] Patent Number: 4,465,073

[45] Date of Patent: Aug. 14, 1984

[54] APPLIANCE FOR WAX DEPILATION, ESPECIALLY FOR FACIAL USE

[75] Inventor: Pierre Schwob, Lyons, France

[73] Assignee: SEB S.A., Selongey, France

[21] Appl. No.: 326,397

[22] Filed: Dec. 1, 1981

[30] Foreign Application Priority Data

Dec. 12, 1980 [FR] France ............................... 80 26370

[51] Int. Cl.³ ............................................. A61B 17/00

[52] U.S. Cl. ......................................... 128/355; 401/2; 401/179; 222/146 HE

[58] Field of Search ............... 128/355; 401/1, 2, 176, 401/179; 222/146 H, 146 HE

[56] References Cited

U.S. PATENT DOCUMENTS 2,642,606 6/1953 Aschenbach ........................ 401/176
3,232,509 2/1966 Newton .
3,298,572 1/1967 Newton .................................. 401/1
3,337,093 8/1967 Newton .
3,858,985 1/1975 Fiveash ........................... 128/355 X
4,032,046 6/1977 Elliott et al. ............................ 401/2

FOREIGN PATENT DOCUMENTS 1459825 10/1966 France .
2155953 5/1973 France .

*Primary Examiner*—Michael H. Thaler
*Attorney, Agent, or Firm*—Young & Thompson

[57] ABSTRACT

The appliance for wax depilation especially of the face comprises a magazine for receiving a block of wax, a tubular duct extending between the magazine and a nozzle having an external opening located at the tip of the outer casing of the appliance. The nozzle is intended to be moved to a point at which it is held in close proximity to the user's skin. A heater adjacent to the duct melts the wax which is engaged within the duct. A carriage for receiving the block of wax within the appliance is intended to be pushed by hand towards the duct by means of an external thumb control button.

7 Claims, 4 Drawing Figures

APPLIANCE FOR WAX DEPILATION, ESPECIALLY FOR FACIAL USE

This invention relates to an appliance for wax depilation, especially for facial use.

It is known that the method of wax depilation is in widespread use, especially for the removal of hairs from legs.

This method consists in melting the wax, in applying it to the leg in the molten state by means of a spatula, for example, in allowing the wax to solidify, then in exerting a pull on the wax in order to detach it from the skin. The hairs which are imprisoned in the wax are thus detached from the skin at the same time as the wax.

This method cannot readily be employed for depilating the face by the user's own unaided efforts. The surface of the face is in fact very irregular and entails the need for a very high degree of accuracy of application of the wax in order to prevent any contact between this latter and very sensitive organs such as the mouth, the nostrils and the eyes.

One type of appliance which is already known serves to heat the wax or like material and to extrude this latter through an outlet nozzle. This apparatus comprises a kind of piston which is displaced by hand at one end of the appliance in order to discharge the wax in paste form within the appliance at the other end of this latter.

This appliance cannot readily be applied to self-depilation of highly localized and sensitive areas of the skin and especially of the face.

The aim of the present invention is to create an appliance for wax depilation which is particularly suitable for this purpose.

The appliance contemplated by the invention for wax depilation especially of the face comprises a magazine for receiving a block of wax, a tubular duct extending between said magazine and a nozzle having its opening at the exterior of the appliance, said nozzle being intended to be moved to a point at which it is held in close proximity to the user's skin, and heating means adjacent to said duct for melting the wax which is engaged within said duct.

In accordance with the invention, said appliance essentially comprises a carriage for receiving the block of wax, said carriage being displaceable by hand in the direction of the duct.

Thus, when the appliance is in service, the user pushes the carriage forward and causes a certain quantity of wax to be discharged from the nozzle by extrusion, for example in the form of a flat strip in the state of paste which can be applied with accuracy on a localized zone of small area of the face.

The user may consequently carry out a very accurate depilation of the face without any attendant hazard to the eyes, the mouth and other sensitive parts of the face.

The above-mentioned carriage can be displaced by the user by actuating a thumb control button which is attached to the carriage and projects outwards from the appliance.

By regulating the effort exerted on said thumb control button, the rate of extrusion of the wax from the outlet nozzle of the appliance can accordingly be controlled with accuracy.

In a preferred embodiment of the invention, provision is made at the inlet of the tubular duct for a sleeve of flexible plastic material which does not adhere to the wax. Said sleeve is provided with means for preventing any backward movement of the block of wax when the carriage is released.

Preferably, said sleeve is provided on its internal surface with a flexible annular lip defining a substantially frusto-conical surface which is widened-out towards the inlet of the sleeve, the smallest diameter of said frusto-conical surface being slightly smaller than the diameter of the wax cartridge.

Other features of the invention will be more apparent upon consideration of the following description and accompanying drawings, wherein.

Figure 1:
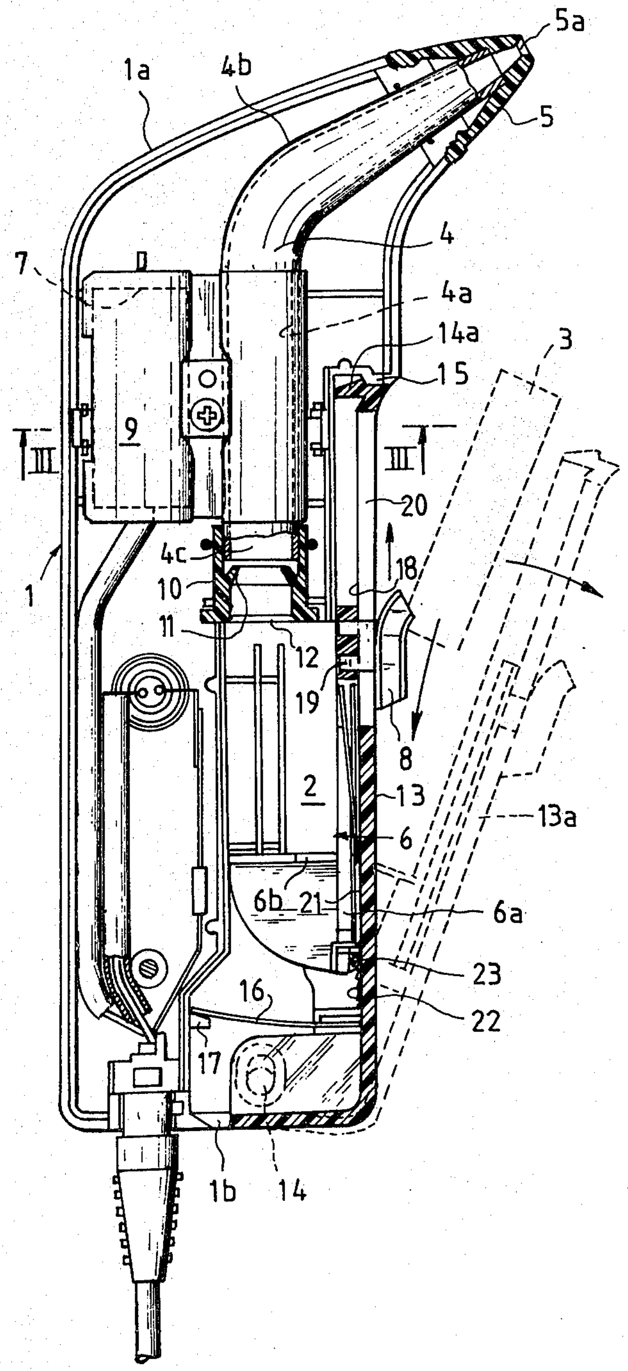
FIG. 1 is an elevation view, partly in longitudinal section, showing the interior of a depilating appliance in accordance with the invention.

In the embodiment shown by way of example in the accompanying figures, the appliance for wax depilation, especially for facial use, comprises an outer casing 1 of plastic material constituted by two half-shells assembled together in the longitudinal direction. Said casing 1 contains a magazine 2 for receiving a block of depilating wax in the form of a cylindrical cartridge 3 (as shown in FIGS. 1 and 4), a cylindrical duct 4 which extends between the magazine 2 and a substantially frusto-conical nozzle 5 having its opening at the exterior of the appliance, a carriage 6 for engaging the cylindrical cartridge 3 within the duct 4 and pushing said cartridge towards the nozzle 5 and a thermistor 7 placed in thermal contact with the duct 4 in order to heat and bring the wax engaged within the duct 4 to a temperature of the order of 60° C.

The carriage 6 is manually displaceable by the user in the direction of the duct 4 by means of a thumb control button 8 which projects outwards from the casing 1. Said carriage 6 is provided at the rear end 6*a* with a heel plate 6*b* constituting a bearing surface for the cartridge 3.

Figure 4:
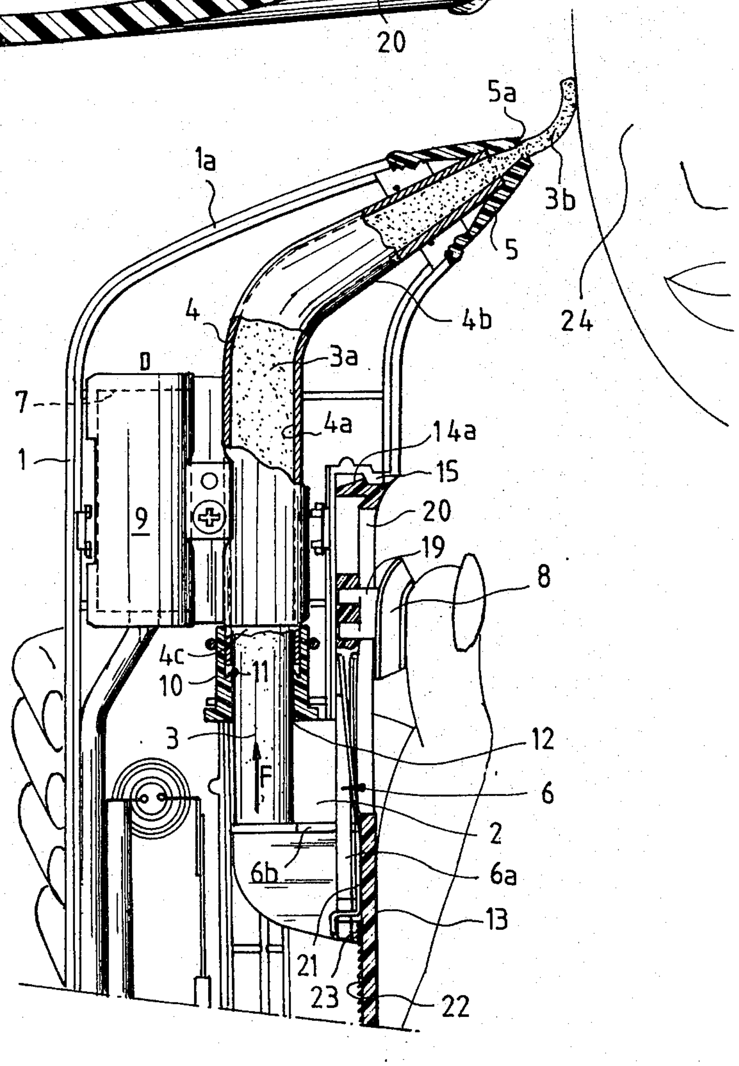
FIG. 4 is a fragmentary view in elevation and in longitudinal section showing the appliance during use.

The casing 1 has a generally oblong shape so as to permit handling by the user as indicated in FIG. 4.

The axis of the nozzle 5 is inclined with respect to the longitudinal axis of the casing 1. The end of the casing 1 adjacent to the nozzle 5 has a shape which is adapted to the angle of inclination of the axis of the nozzle 5.

The cylindrical duct 4 is of metal having good thermal conductivity such as aluminum in order to permit excellent heat exchange with the thermistor 7.

The portion 4*a* of the cylindrical duct 4 which is adjacent to the thermistor 7 extends in the direction of the longitudinal axis of the casing 1. Said portion 4*a* of the cylindrical duct 4 is joined by means of an elbow to an inclined portion 4*b* which opens to the exterior via the nozzle 5.

Said nozzle 5 is advantageously formed of flexible plastic material such as silicone which is nonadhesive with respect to wax. Said nozzle 5 is removably mounted on the end l*a* of the casing 1. It is an advantage to be able to make use of a number of interchangeable nozzles 5 in which the discharge orifices 5*a* have different cross-sectional areas. Thus, depending on the cross-sectional area of the nozzle 5, it is possible to obtain at the outlet of said nozzle a flat strip of greater or smaller thickness or a cylindrical strip of wax in paste form of greater or smaller diameter.

The portion 4*a* of the duct 4 has an internal diameter corresponding substantially to the diameter of the wax cartridge 3 which is placed within the magazine 2 along the axis of said duct 4.

Figure 3:
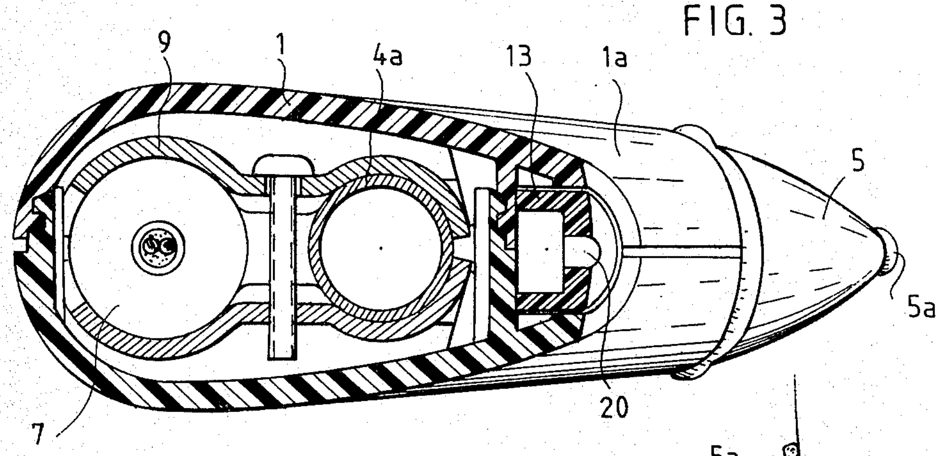
FIG. 3 is a sectional view taken along the plane III—III of FIG. 1.

Thermal contact between the thermistor 7 and the portion 4*a* of the duct 4 is achieved by means of two metallic half-shells 9 which cover the thermistor 7 and the portion 4*a* of the duct 4 in such a manner as to follow the profile of these latter (as shown in particular in FIG. 3).

At the inlet 4*c* of the cylindrical duct 4, there is placed a sleeve 10 of flexible plastic material such as silicone which is nonadhesive with respect to the wax. Said sleeve 10 is provided on its internal surface with a flexible annular lip 11 and this latter defines a frusto-conical internal surface which is widened-out towards the inlet orifice 12 of said sleeve 10. The smallest diameter of said frusto-conical surface is slightly smaller than the diameter of the wax cartridge 3.

As shown in FIG. 1, the magazine 2 is closed by a cover 13 which is hinged on a pivot 14, said pivot being mounted at the end 1*b* of the casing 1 which is remote from the discharge nozzle 5. When the cover 13 is opened, it occupies the broken-line position 13*a* indicated in FIG. 1.

In the closed position as shown in FIG. 1, the cover 13 is locked to the casing by means of a nose 14*a* formed on the edge of the cover opposite to the articulation 14, said nose 14*a* being engaged by snap-fastening on a boss 15 formed on the casing 1. Said locking action takes place in opposition to the action of a spring 16 which is attached to the cover 13 in the vicinity of the pivot 14, said spring being applied against a stop 17 formed within the interior of the casing 1.

Figure 2:
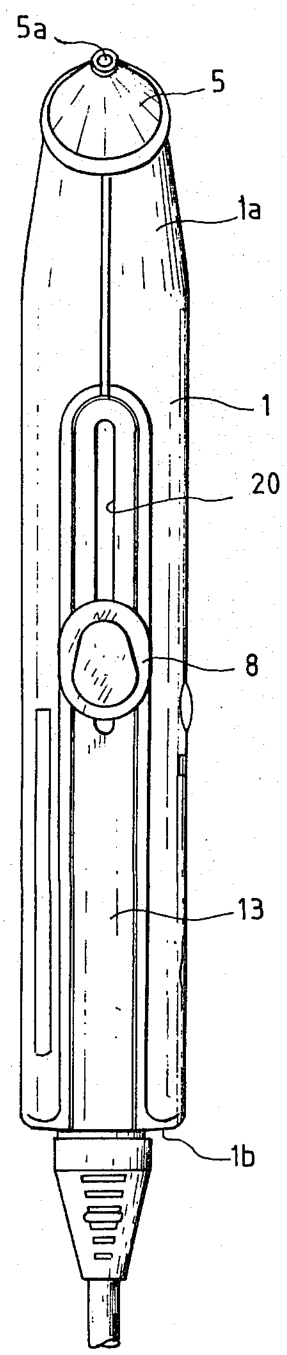
FIG. 2 is an elevation view taken at right angles to FIG. 1 and showing in particular the magazine cover of the appliance.

It is apparent from FIGS. 1 and 2 that, in the closed position, the external surface of the cover 13 is located substantially in the plane of extension of the external surface of the casing 1.

In addition, the internal surface 18 of the cover 13 is adapted to support the carriage 6 and the members for guiding this latter as it is displaced towards the cylindrical duct 4.

In the example shown (in FIGS. 1 and 4), guiding of the displacement of the carriage 6 is performed by means of a lug 19 engaged within a slot 20 (as also shown in FIG. 2) formed in the cover 13 along the longitudinal axis of the casing 1. Said lug 19 is joined on the one hand to the carriage 6 and on the other hand to the thumb control button 8 which projects from the cover 13.

A blade spring 21 is mounted between the carriage 6 and the cover 13 behind the thumb control button 8. Said spring tends to move the rear portion 6*a* of said carriage 6 away from the cover 13 (as shown in FIGS. 1 and 4).

Furthermore, in the example which is illustrated, the cover 13 is provided on its internal face 18 with a toothed rack 22 in cooperating relation with a retaining catch 23 fixed on the rear portion 6*a* of the carriage 6 in order to prevent this latter from moving forward when an abnormal thrust is exerted on the thumb control button 8.

The operation of the depilating appliance described in the foregoing will now be explained.

Before using the appliance, the wax cartridge 3 is placed within the magazine 2. To this end, the cover 13 is unlocked by pushing it downwards to a slight extent in order to release the nose 14*a* from the boss 15, whereupon the cover is opened and then moved to the position 13*a* shown in FIG. 1.

The carriage 6 is placed in the bottom position or in other words in the position in which it is located at the maximum distance from the inlet of the duct 4 by displacing the thumb control button 8 in the downward direction as shown in FIG. 1. A cartridge 3 is then placed on said carriage and the cover 13 is closed.

The supply of electric current to the thermistor 7 is initiated. The cartridge 3 is engaged within the cylindrical duct 4 by pushing the carriage 6 in the direction of the arrow F of FIG. 4. As it engages within the sleeve 10, the cartridge 3 causes outward withdrawal of the flexible lip 11.

The wax 3*a* contained in the duct 4 is heated to a temperature of the order of 60° C. At this temperature, the wax 3*a* is in a sufficiently fluid state to undergo extrusion through the orifice 5*a* of the nozzle 5 when displacing the carriage 6 towards the duct 4 by pushing the thumb control button 8 in the forward direction.

The wax 3*a* is discharged from the nozzle 5 in the form of either a flat strip or a cylindrical strip 3*b* of wax in paste form which the user applies to the skin 24 of the face at the precise point at which depilation is to be performed.

When the user has applied the desired quantity of wax 3*b* on the skin to be depilated, the thumb control button 8 may then be released. Backward return of the cartridge 3 engaged within the sleeve 10 is prevented by anchoring of the lip 11 of the sleeve 10 by reason of the fact that said lip has penetrated into the wax while this latter has a semiplastic consistency.

At the end of travel of the carriage 6, the cartridge 3 is fully engaged within the duct 4. Should it be desired to continue to use the appliance, it is then only necessary to insert a fresh wax cartridge 3 in the magazine 2.

Experience has shown that the depilating appliance in accordance with the invention is particularly convenient to use. It is in fact possible by means of this appliance to apply the wax on the skin with a very high degree of accuracy and in perfectly regulated quantities, thus permitting depilation of the skin in very small but sensitive areas in the vicinity, for example, of the user's mouth, nostrils or eyes. Furthermore, the appliance in accordance with the invention prevents the hot wax from coming into contact with the user's hands. In addition, by reason of the fact that the heating temperature of the wax is controlled by a thermistor 7, the user is in no way liable to suffer from skin burns as a result of overheating of the wax.

It is also worthy of note that the appliance in accordance with the invention does not entail the need for any maintenance or cleaning. Thus the wax which remains within the duct 4 and solidifies therein after use need not be removed from the appliance. In fact, any wax which may thus be present within the appliance is wholly protected against any external dust particles and may therefore be re-melted and used again.

As will readily be understood, the invention is not limited to the example described in the foregoing and many modifications may therefore be contemplated without thereby departing either from the scope or the spirit of the invention.

Thus the magazine 2 could be adapted to contain a number of wax cartridges which may thus be engaged successively within the duct 4.

It is also apparent that the appliance in accordance with the invention is not limited to depilation of facial skin but may be employed for other areas of the skin.

The appliance in accordance with the invention could also be employed for depilating legs on condition that its dimensions are adapted to meet this application by reason of the relatively large quantities of wax required for depilation of legs.

The thermistor 7 can be replaced by a conventional electric heating resistor which may be associated with a thermostat in order to regulate the heating temperature of the wax.

What is claimed is:

1. In an appliance for wax depilation comprising a tubular duct (4) for receiving a block of wax (3) communicating with a nozzle (5) having an opening at the exterior of the appliance, said nozzle being adapted to be moved in close proximity to the user's skin, heating means (7) adjacent to the tubular duct (4) for melting wax (3) within said duct (4), and movable means **(6*b*) to bear against the rear face of the block of wax (3) to push the latter toward the nozzle (5); the improvement in which said movable means are arranged in a magazine (2) and are comprised by a heel plate (6*b*) fixed to a carriage (6), said appliance comprising further a lateral cover (13)** for closing said magazine and for introducing into said magazine a block of wax, a casing which contains said magazine, said cover being pivotally mounted on said casing, the cover supporting and guiding said carriage during movement of the carriage toward the nozzle, and means carried by the cover outside the cover for moving the carriage toward the nozzle.

2. An appliance according to claim 1, wherein the carriage is rigidly fixed to a thumb control button which projects outward from the appliance.

3. An appliance according to claim 1, wherein the tubular duct is of metal and wherein the heating means comprises a thermistor in thermal contact with said tubular duct.

4. An appliance according to claim 1, the external surface of said cover being located substantially in the plane of extension of the external surface of the casing of the appliance when said cover is in the closed position.

5. An appliance according to claim 1, wherein said carriage is guided by a slot formed in the cover, and a lug which is engaged in said slot and which is connected to the carriage and to an external thumb control button.

6. An appliance according to claim 1, said casing (1) having a generally elongated shape to permit handling by the user, a part **(4*a*) of the duct (4) which is adjacent to said heating means (7) extending in the direction of the length of said casing (1) and the carriage (6)** being guided to be movable along said direction.

7. Appliance according to claim 6, wherein the axis of the nozzle (5) forms an angle of inclination with the length of the casing (1).

* * * * *